(12) United States Patent
Ingelmann et al.

(10) Patent No.: US 11,293,874 B2
(45) Date of Patent: Apr. 5, 2022

(54) ANALYSIS DEVICE FOR DETERMINING A MEASURAND REPRESENTING A SILICATE CONCENTRATION IN A SAMPLE LIQUID

(71) Applicant: Endress+Hauser Conducta GmbH+Co. KG, Gerlingen (DE)

(72) Inventors: Michael Ingelmann, Vaihingen an der Enz (DE); Ralf Steuerwald, Eberdingen (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 130 days.

(21) Appl. No.: 16/276,747

(22) Filed: Feb. 15, 2019

(65) Prior Publication Data
US 2019/0257848 A1 Aug. 22, 2019

(30) Foreign Application Priority Data
Feb. 16, 2018 (DE) ..................... 10 2018 103 530.6

(51) Int. Cl.
*G01N 21/78* (2006.01)
*G01N 33/18* (2006.01)
(Continued)

(52) U.S. Cl.
CPC ......... *G01N 21/78* (2013.01); *G01N 21/3577* (2013.01); *G01N 33/182* (2013.01); *G01N 35/1095* (2013.01)

(58) Field of Classification Search
CPC .. G01N 21/78; G01N 33/182; G01N 21/3577; G01N 35/10; G01N 35/1002; G01N 35/1095
See application file for complete search history.

(56) References Cited

U.S. PATENT DOCUMENTS 5,363,874 A * 11/1994 Henszey .............. G01N 1/2035
137/14
5,550,053 A * 8/1996 Salpeter ............... G01N 21/274
250/252.1
(Continued)

FOREIGN PATENT DOCUMENTS

CN 1653339 A 8/2005
CN 1656275 A 8/2005
(Continued)

OTHER PUBLICATIONS

Hach, Installation Guide for 5500sc Si)2, Edition 2 (Year: 2016).*
(Continued)

*Primary Examiner* — Justin N Olamit
(74) *Attorney, Agent, or Firm* — Christopher R. Powers; Endress+Hauser (USA) Holding Inc.

(57) ABSTRACT

The present disclosure includes to an analysis device for determining a measurand representing a silicate concentration in a sample liquid, including a housing divided into an electronics region and a fluidic region, wherein the electronics region is separated from the fluidic region by at least one wall. In the fluidic region are a measuring cell, a sample feed line connected to the measuring cell, at least one liquid container having a liquid therein and connected to the measuring cell via a liquid line, and at least one pump configured to transport at least a portion of the liquid from the liquid container into the measuring cell, in which the sample feed line is connected to an over-pressurized container containing the sample liquid, where the container is arranged outside the housing. The electronics region includes an electronic control system configured to control the operation of the analysis device.

11 Claims, 2 Drawing Sheets

(51) Int. Cl.
   *G01N 35/10*     (2006.01)
   *G01N 21/3577*   (2014.01)

(56) References Cited

U.S. PATENT DOCUMENTS

| | | | | |
|---|---|---|---|---|
| 6,460,406 | B1 * | 10/2002 | Drain | G01N 21/15 |
| | | | | 356/440 |
| 8,268,248 | B2 * | 9/2012 | Steuerwald | G01N 21/253 |
| | | | | 422/82.05 |
| 9,086,156 | B2 * | 7/2015 | Zachmann | G01N 35/1097 |
| 9,772,287 | B2 * | 9/2017 | Al-Moniee | G01N 21/6486 |
| 9,945,830 | B2 * | 4/2018 | Feng | G01N 27/4163 |

FOREIGN PATENT DOCUMENTS

| | | | |
|---|---|---|---|
| CN | 100541173 C | 9/2009 | |
| CN | 101813704 A | 8/2010 | |
| CN | 102226755 A | 10/2011 | |
| CN | 102778575 A | 11/2012 | |
| EP | 0474607 A2 * | 3/1992 | G01N 1/10 |

OTHER PUBLICATIONS

Hach, Measurement of Silica in the Steam/Water Cycle and Demineralisation Plants, 4 pp.

* cited by examiner

ANALYSIS DEVICE FOR DETERMINING A MEASURAND REPRESENTING A SILICATE CONCENTRATION IN A SAMPLE LIQUID

CROSS-REFERENCE TO RELATED APPLICATION

The present application is related to and claims the priority benefit of German Patent Application No. 10 2018 103 530.6, filed on Feb. 16, 2018, the entire contents of which are incorporated herein by reference.

TECHNICAL FIELD

The present disclosure relates to an analysis device for determining a measurand representing a silicate concentration in a sample liquid—in particular, in an aqueous solution.

BACKGROUND

The concentration of silicate in a sample liquid—in particular, in water—is an important parameter in the field of ultrapure water treatment and in steam/water circuits in power plants. Dissolved silicate—also referred to as silica—can, for example, lead in power plant systems to acid-resistant deposits which may affect the thermal efficiency of the systems. If, for example, silicate deposits form in turbines, this can lead in the worst case to damage which can impair the operation of the system or possibly even lead to an interruption in operation.

Automatic analysis devices are used to monitor the silicate content in a liquid—hereinafter also referred to as sample liquid. These devices are configured to determine a measurand representing a concentration of silicate in the sample liquid in an automated, wet chemical method. A measurand representing the concentration of silicate in the sample liquid is understood here to mean, in particular, a measurand that is dependent upon this concentration, e.g., the silicate concentration, a silicate activity, or a mass or volume percentage of silicate. For the automated performance of measurements, the analysis devices possess a fluidic unit which is used to dose and handle reaction components (reagents) used in the wet chemical method, a sensor for generating measurement signals that are dependent upon the measurand, and an electronic control system which controls the components of the fluidic unit, e.g., valves, and the sensor for performing the measurements, and may additionally be designed to process the measurement signals. The electronic control system comprises a data processing device with processors and data memories, e.g., a computer or measuring transducer. One or more computer programs executable by the data processing device are stored in the latter and used for the automated control of the measurements and the determination of measured values. The fluidic unit, the liquid containers with reagents to be added to the sample, and the electronic control system are typically housed in a cabinet-like housing.

A measuring cycle of such an analysis device can run in the following manner, for example. First, a sample feed line of the analysis device is connected to a container containing the sample liquid of a system, e.g., a boiler or a liquid line. In a measuring cell, the analysis device mixes a predetermined volume of the sample liquid taken from the container via the sample feed line with predetermined volumes of one or more liquid reagents. In the reaction mixture thus obtained, a chemical reaction occurs in which a colored reaction product is produced. In order to determine a silicate concentration, silicate ions can, for example, first be converted to silicomolybdic acid complexes and then reduced to a blue-colored heteropoly acid (so-called heteromolybdenum blue method). Based upon an optical measurement, e.g., an absorption measurement, the analysis device determines the intensity of the color of the reaction mixture. This is a measure of the concentration of the colored reaction product contained in the reaction mixture, which in turn is a measure of the silicate concentration in the sample liquid. From measurement signals of the absorption measurement, the data processing device of the analysis device calculates measured values of the measurand in the unit of the measurand on the basis of calibration data stored in a memory of the data processing device, e.g., a stored calibration function or calibration table, and outputs the measured values determined.

A special feature in the measurement of the silicate concentration in sample liquids in typical applications in the power plant and/or ultrapure water field by means of automatic analysis devices is that the sample liquids to be monitored are generally under pressure, and thus also reach the sample feed line of the analysis devices under pressure.

A conventional automatic analysis device for measuring the silicate concentration is known from the brochure, "Measuring the silica content in the steam/water circuit and demineralization systems" by the supplier, Hach Lange. In this analysis device, the sample liquid passes, by means of the overpressure prevailing in the container from which it is taken, via the sample feed line into a measuring cell for absorption measurement. The reagents to be added to the sample liquid are also conveyed from liquid containers, in which the reagents are held, by means of a pressure supply system and transported via liquid lines into the measuring cell. The analysis device thus does not have any pumps.

However, in such a liquid transport, by applying an overpressure to the reagent containers or conveying the liquid sample under pressure, there is a safety risk due to the pressurized lines and liquid containers. If a container or a line has a mechanical weak point or a leak, liquid can pass from the container into the interior of the housing of the analysis device during operation of the analysis device. This can lead to damage to other device components arranged in the housing, for example, by contact of the components with the partially corrosive liquids. This is particularly problematic when escaping liquid reaches sensitive electronic parts, e.g., the electronic control system, and causes a short circuit there, for example.

SUMMARY

The aim of the present disclosure is therefore to specify an analysis device for measuring a measurand that is dependent upon a silica concentration in a sample liquid, which analysis device does not have these disadvantages. In particular, the risk of damage to electronic parts by liquids, or gases or vapors, escaping inadvertently from liquid lines or liquid containers is to be avoided in this analysis device.

The aim is achieved by an analysis device according to claim 1. Advantageous embodiments are listed in the dependent claims.

The analysis device according to the present disclosure for determining a measurand representing a silicate concentration in a sample liquid, e.g., water or ultrapure water, comprises: a housing divided into an electronics region and a fluidic region, wherein the electronics region is separated from the fluidic region by at least one wall; a measuring cell arranged within the fluidic region; a sample feed line arranged within the fluidic region and opening into the measuring cell, wherein the sample feed line is connected to an over-pressurized container containing the sample liquid, wherein the container is arranged outside the housing; at least one liquid container containing a liquid and arranged within the fluidic region; a liquid line which is arranged within the fluidic region, opens into the measuring cell, and is connected to the at least one liquid container; at least one pump arranged within the fluidic region and configured to transport at least a portion of the liquid from the first liquid container through the liquid line into the measuring cell; an optical sensor arranged within the fluidic region and having a radiation source and a radiation receiver, wherein the radiation source and the radiation receiver are arranged with respect to the measuring cell in such a way that measuring radiation emitted by the radiation source passes through the measuring cell and impinges on the radiation receiver; and an electronic control system which is arranged within the electronics region, is electrically connected to a drive of the at least one pump, to the radiation source, and to the radiation receiver and is configured to control the drive of the at least one pump for transporting liquid from the first liquid container into the measuring cell, to operate the radiation source for emitting measuring radiation, to detect electrical signals generated by the radiation receiver, and to determine values of the measurand on the basis of the signals of the radiation receiver.

The pump can be designed, for example, as a diaphragm pump or as a peristaltic pump. The liquid line can be designed, for example, as a hose line, on which the pump, e.g., the peristaltic pump, acts in order to transport liquid through the liquid line. In another embodiment, the pump may be designed as a syringe pump, which can be connected to the liquid container for removing a predetermined amount of liquid and to the liquid line for supplying the extracted amount of liquid to the measuring cell.

The radiation source and the radiation receiver can be arranged on opposite sides of the measuring cell, for example. Alternatively, they can also be arranged on the same side of the measuring cell, wherein, after passing through at least a part of the measuring cell, the measuring radiation is reflected on a reflector, e.g., a reflecting wall of the measuring cell or an additional mirror. The radiation receiver can also be arranged in such a way that it can receive measuring radiation that is scattered or reflected in the measuring cell.

The signals of the radiation receiver can be analog or already-digitized signals.

By the housing of the analysis device being divided into an electronics region and a fluidic region separated therefrom by means of a wall, and by arranging fluidic components, such as liquid containers, liquid lines, and pumps, as well as the measuring cell, within the fluidic region, while the sensitive electronic components—in particular, the electronic control system—are arranged outside the fluidic region in the electronics region, the risk of damage by liquid, which can escape from the sample feed line transporting the sample liquid under pressure in the event of damage, is avoided or at least significantly reduced. In an advantageous embodiment, the wall can separate the fluidic region in a liquid-tight or splash-proof manner from the electronics region. By conveying liquids from the liquid containers present in the housing by means of pumps instead of by means of a pressure supply system which applies an over-pressure to the liquid containers, the risk of liquid escaping from the liquid containers or from liquid lines from and to the liquid containers is avoided.

The analysis device can comprise several liquid containers containing one liquid each, wherein all liquid containers of the analysis device are arranged within the fluidic region, and wherein the liquid containers are respectively connected to the measuring cell via a liquid line extending within the fluidic region. In this way, all liquid containers of the analysis device and the liquid lines connected thereto are arranged within the fluidic region, and thus separate from the device electronics to be protected. In an advantageous embodiment, a pump arranged in the fluidic region can be assigned to each of the liquid lines connecting the liquid containers arranged within the fluidic region to the measuring cell such that the pump assigned to a liquid line is used to transport liquid through the liquid line. By conveying the transport of all liquids used in the analysis device, with the exception of the pressurized sample liquid on the system side, by means of pumps instead of by overpressure, there is a considerably smaller risk of liquid escaping from the lines or containers into the interior of the housing.

The liquid containers can contain various reagents to be supplied to the sample liquid for determining the silicate concentration. At least one or more liquid containers may contain rinsing or cleaning liquids. One of the liquid containers of the analysis device can contain a standard solution containing silicate in a predetermined concentration, wherein a pump, which is assigned to the liquid line connecting this liquid container to the measuring cell for transporting the standard solution into the measuring cell, is designed as a peristaltic pump. The standard solution is used to calibrate the analysis device. To this end, the control system can perform a calibration measurement between two measurements, in which calibration measurement standard solution is conveyed into the measuring cell instead of the sample liquid, the reagents are added to the standard solution, and a measured value of the silicate concentration in the standard solution is determined on the basis of an optical measurement. A calibration can be carried out by comparing the known concentration of the standard solution with the determined silicate concentration. Since larger amounts of the standard solution must be delivered than of the reagents, the use of a peristaltic pump which can continuously convey the liquid is advantageous for the transport of the standard solution. Of course, another type of pump can also be used.

In one embodiment, the analysis device further comprises a sample discharge line arranged within the fluidic region and opening into the measuring cell. The sample discharge line can be connected to a liquid container for receiving liquid discharged from the measuring cell. The discharged liquid may, for example, be a spent reaction mixture or an excess of sample liquid or of standard solution.

The measuring cell can have an overflow which communicates with the sample discharge line and determines a maximum fill-level of the measuring cell—in particular, such that, when the maximum fill-level in the measuring cell is reached, liquid passes from the measuring cell via the overflow into the sample discharge line.

The sample feed line may comprise a valve that is used to selectively open or block the sample feed line for the flow of the sample liquid. This allows switching between different sample input channels.

In a further embodiment, a pressure reducer can be arranged fluidically between the sample feed line and the container containing the sample liquid. This ensures that no excessively intensive pressure peaks can reach the device, which could cause detachment of the connection of the liquid lines forming the sample feed line to interconnected components, such as valves, or to the measuring cell. This is another safety measure to prevent liquid from escaping into the housing interior of the analysis device. A flow-measuring device—in particular, a flow meter—which is configured to detect a flow of the sample liquid through the sample feed line, can be arranged within the sample feed line. This flow meter is used to monitor the proper operation of the analysis device.

In a possible further embodiment of the analysis device, the pressure reducer may be controlled on the basis of the measurement signal of the flow meter. For example, the electronic control system of the analysis device may be configured to control the pressure reducer on the basis of the measurement signal of the flow meter.

A portion of the sample feed line may extend through a heater arranged within the fluidic region of the housing. The heater is used to preheat the sample liquid before introduction into the measuring cell.

BRIEF DESCRIPTION OF THE DRAWINGS

The present disclosure is explained in detail below with reference to the exemplary embodiment shown in the figures. Shown are.

DETAILED DESCRIPTION

Figure 1:
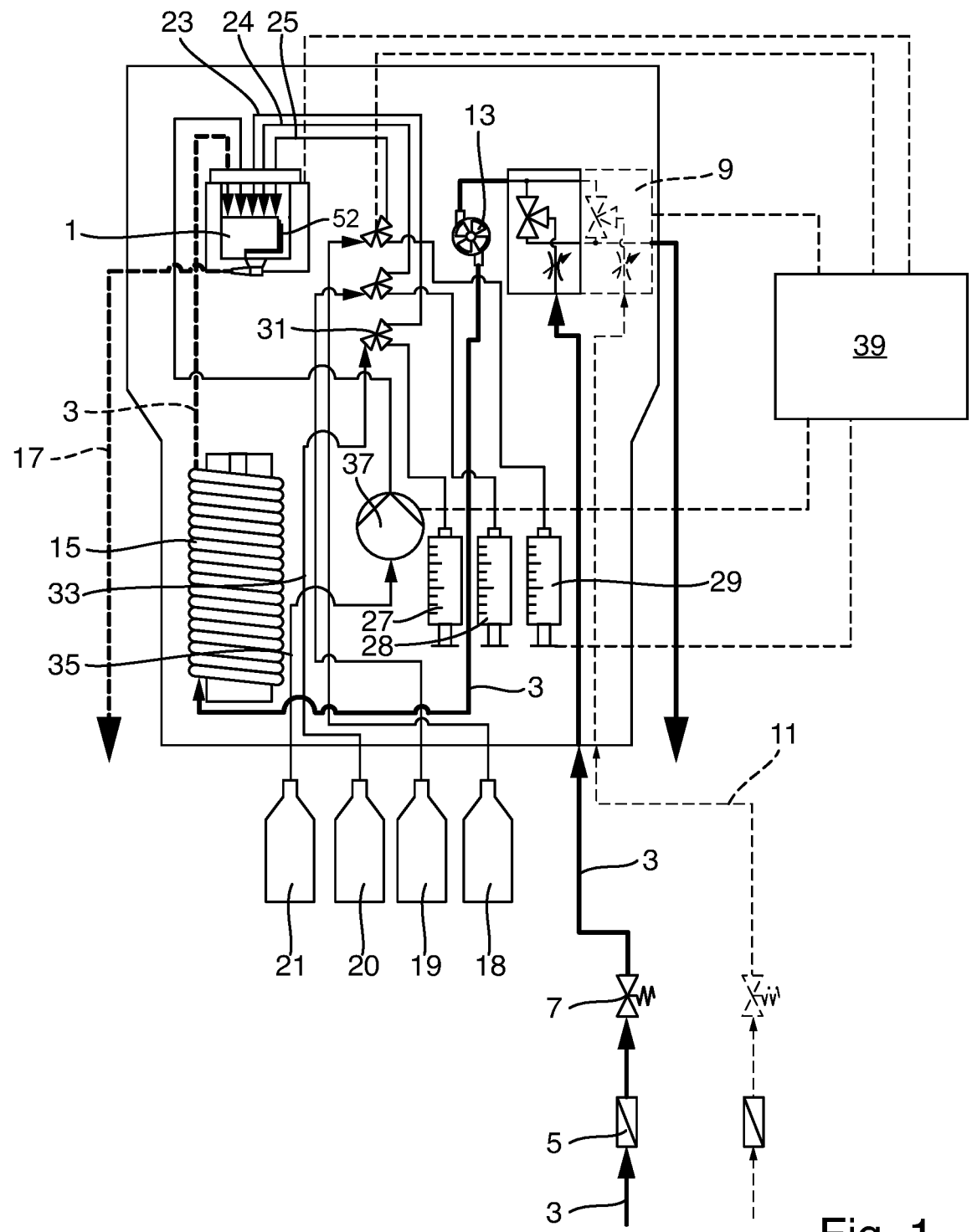
FIG. 1 shows a schematic illustration of the structure of an analysis device according to an exemplary embodiment.

FIG. 1 schematically shows the structure of an analysis device for measuring a silicate concentration in a sample liquid. The illustration is used to illustrate the functionality and the interaction of the individual components of the analysis device; the components are therefore not shown true to scale.

The analysis device has a reaction chamber which is simultaneously used as a measuring cell 1 for absorption measurements. The measuring cell 1 is connected via a sample feed line 3 to an over-pressurized container (not shown in FIG. 1), in which the sample liquid to be examined is contained. The sample liquid is transported through the sample feed line 3 by means of the overpressure prevailing in the container; no pump is therefore provided in the sample feed line 3. The container can, for example, be a line or a boiler of a technical installation. Arranged in the sample feed line 3 is a filter 5, downstream of which a pressure reducer 7 is arranged fluidically. Downstream of the pressure reducer 7, a valve device 9 is arranged, by means of which the sample feed line 3 can be interrupted, e.g., in order to switch to a second sample channel 11. A flow meter 13 is arranged fluidically downstream of the valve device 9. Upstream of the measuring cell 1 is arranged a portion, heatable by means of a heater 15, of the sample feed line 3. The heater 15 of the liquid flowing in the sample feed line in this portion may be realized, for example, by means of a heat exchanger or by means of a resistance heater. Into the measuring cell 1 also opens a sample discharge line 17, which may, for example, be connected to a collecting container for spent liquids arranged outside the analysis device.

The analysis device has several liquid containers 18, 19, 20, 21. Three of the liquid containers 18, 19, 20 contain three reagents which are intended to be added successively to the sample liquid presented in the measuring cell 1, in order to form a blue-colored, photometrically-determinable reaction product from silicate contained in the sample liquid. The reagents include molybdate anions, sulfuric acid, and a reducing agent, e.g., metol (4-(methylamino)phenol sulfate). The last liquid container 21 contains a standard solution, which contains a known concentration of silicate and is used to calibrate the analysis device.

The liquid containers 18, 19, 20, which contain reagents, are each connected to the measuring cell via a separate liquid line 23, 24, 25. A syringe pump 27, 28, 29 is assigned to each of these liquid lines such that each syringe pump transports a reagent through its assigned liquid line into the measuring cell. This is specifically realized in the manner described below with reference to the syringe pump 27 assigned to the liquid line 23. The syringe pump 27 can be connected via a valve 31 in a first valve position to the liquid line 33 opening into the liquid container 20. In a second valve position, the valve 31 can connect the syringe pump 27 to the liquid line 23 opening into the measuring cell. If the valve 31 is in the first position, the syringe pump 27 can aspirate liquid from the liquid container 20. If the valve 31 is in the second position, the syringe pump 27 can transport the aspirated liquid into the measuring cell 1.

The liquid container 21 is connected to the measuring cell via a liquid line 35. The liquid line 35 is designed as a flexible hose line, and the pump 37 assigned to it for transporting the standard solution from the liquid container 21 into the measuring cell is designed as a peristaltic pump. So that undesired entrainment between the sample liquid and the standard liquid contained in the liquid container 21 cannot occur, the liquid line 35 is guided into the measuring cell 1 separately from the sample feed line 3.

The transport of all liquids serving to determine the silicate concentration, including calibration standard liquids and, optionally, additional cleaning liquids, with the exception of the sample liquid itself, is carried out by means of pumps in the analysis device described here. In this way, the occurrence of a marked overpressure in the liquid containers 18, 19, 20, 21, the liquid lines, and the measuring cell 1 is avoided. The risk of liquid escaping into the housing of the analysis device when a leak or mechanical weak points of these components are present is thus substantially reduced.

For detecting photometric measured values correlating with the measurand, the measuring cell 1 comprises an optical sensor with a radiation source (not shown in FIG. 1), which radiates measuring radiation at a wavelength of the range between 800 and 830 nm into the measuring cell 1, and with a radiation receiver (not shown in FIG. 1), which detects the measuring radiation after its passage through the measuring cell 1 and the liquid contained therein. The radiation source may comprise an LED. The radiation receiver may comprise one or more photodiodes and is designed to generate and output an electrical signal dependent upon the intensity of the received radiation. The measuring cell 1 also comprises a heater for heating the sample liquid received in the measuring cell 1, or a reaction mixture received in the measuring cell 1.

The analysis device also has an electronic control system 39, which may comprise a data processing device, e.g., a computer, a measuring transducer, and/or a memory-programmable logic controller. The control system 39 is connected to the drives of the syringe pumps 27, 28, 29 and the peristaltic pump 37, to the valves 9, 31, and to the optical sensor of the measuring cell 1 (not all connections are shown in FIG. 1 for the sake of clarity). The control system 39 is designed to actuate the valves 9, 31 and the pumps 27, 28, 29, 37 according to an operating program which is present in a memory of the control system 39 and can be executed by the control system 39 in order to feed the sample liquid and the reagents from the liquid containers 18, 19, 20 to the measuring cell 1 and mix them there. The control system 39 is further designed to control the optical sensor for detecting measurement signals, to process measurement signals of the optical sensor, and to determine measured values of the silicate concentration in the sample liquid on the basis of the measurement signals. For this purpose, the control system 39 comprises an evaluation program which assigns measured values of the measurand in its physical unit to the measurement signals of the sensor on the basis of stored calibration data.

The control system 39 may be constructed of one or more parts; for example, it may be divided into several units connected to each other for communication. It can have a display and input means which serves as an HMI interface for inputting parameters and queries, and for outputting measured values and other information, such as alarm messages and maintenance and diagnostic information.

A measurement of the silicate concentration in the sample liquid by means the analysis device shown in FIG. 1 comprises the following steps:

In a first step, sample liquid is taken from an overpressurized container of a system to be monitored. To this end, the control system 39 controls the valve device 9 in order to open the sample feed line 3 so that the pressurized sample liquid passes through the sample feed line 3 via the filter 5, the pressure reducer 7, the flow sensor 13, and the heater 15 into the measuring cell 1. The measuring cell 1 has an overflow 52 so that, upon reaching a fill-level of the measuring cell 1 determined by the overflow 52, sample liquid is discharged again from the measuring cell via the sample discharge line 17. This ensures that a precisely predetermined amount of the sample liquid is present in the measuring cell 1.

In a second step, predetermined volumes of the reagents contained in the liquid containers 18, 19, 20 are dosed into the sample liquid presented in the measuring cell 1. To this end, the control system 39 controls drives of the syringe pumps 27, 28, 29 in cooperation with the valves 31 assigned to the syringe pumps 27, 28, 29, in order to measure the predetermined volumes by means of the syringe pumps 27, 28, 29 and to subsequently transport them into the measuring cell 1 via the liquid lines 23, 24, 25 which open into the measuring cell 1 and are assigned to the liquid containers 18, 19, 20. In the measuring cell 1, the reagents and the sample liquid are mixed and heated, wherein a blue-colored heteropoly acid ("silicomolybdenum blue") is formed by chemical reactions from the silicate contained in the sample liquid.

In a third step, a photometric measurement is performed, wherein a measurement signal is generated, which reflects the intensity of the color, caused by the silicomolybdenum blue, of the reaction mixture contained in the measuring cell. To this end, the control system 39 controls the radiation source of the optical sensor for emitting measuring radiation. The measuring radiation passes through at least a part of the measuring cell and in this way reaches the radiation receiver of the optical sensor. The latter generates an electrical measurement signal dependent upon the received radiation intensity. The wavelength of the measuring radiation is dimensioned such that its intensity after passing through the reaction mixture is weakened according to the Lambert-Beer law as a result of interaction with the silicomolybdenum blue contained therein. The intensity received by the radiation receiver and the corresponding electrical signal thus depend upon the concentration of the silicomolybdenum blue in the reaction mixture. Accordingly, the electrical measurement signal is also a measure of the silicate concentration originally present in the sample liquid.

In a fourth step, a measured value of the silicate concentration is determined from the electrical measurement signal of the optical sensor. To this end, the control system 39 assigns a measured value of the concentration in the desired physical unit, e.g., g/L, to the currently-detected electrical measurement signal based upon a stored calibration function or a stored calibration table, and outputs the thus determined measured value via a user interface (display) or a communication interface, via which a connection with an external device, e.g., a process control system or an operating device, is possible.

The spent reaction mixture is subsequently displaced from the measuring cell 1 by rinsing with sample liquid from the sample feed line 3 and discharged via the sample discharge line 17 into a collecting container for spent liquid. The analysis device is then ready for a new measurement.

Figure 2A:
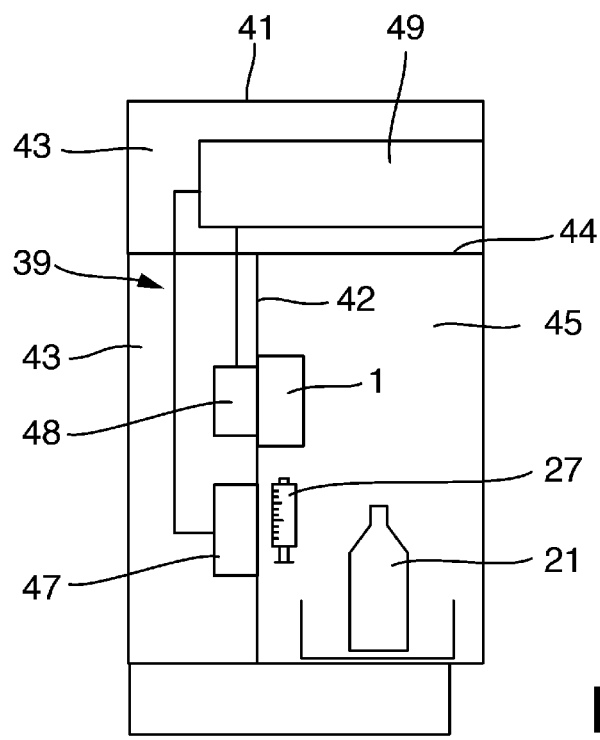
FIG. 2A shows a schematic illustration of the housing of the analysis device shown in FIG. 1, in a longitudinal sectional view seen from the side.
Figure 2B:
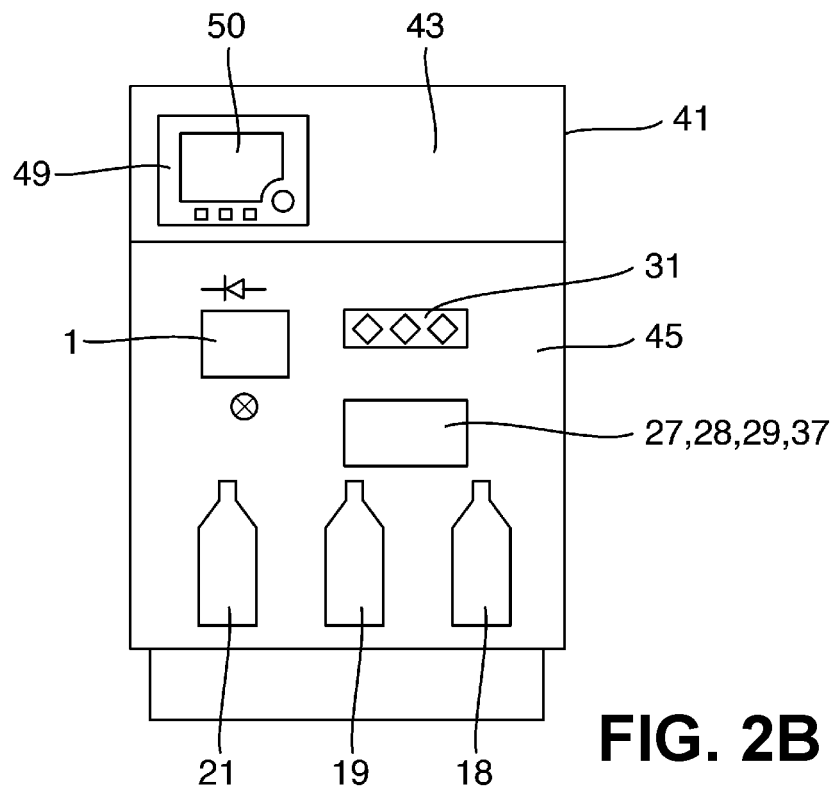
FIG. 2B shows a schematic illustration of the housing of the analysis device shown in FIG. 1, viewed from the front.

FIGS. 2A and 2B schematically show two different views of the housing 41 of the analysis device described above. Some components of the analysis device are schematically shown in the housing 41, for orientation. FIG. 2A shows a longitudinal section through the housing 41 seen from the side; FIG. 2B shows a front view of the housing 41.

The housing 41 is divided into an electronics region 43 and a fluidic region 45. The two regions are separated from one another by walls 42, 44, wherein the electronics region 43 in the exemplary embodiment shown here is again divided into two spaces by the wall 44. However, this is not absolutely necessary. In the fluidic region 45 are arranged all components of the analysis device, which may contain liquids and are used to store, transport, and treat liquids in the context of the analysis method described above. These are, in particular, the liquid containers 18, 19, 20, 21, liquid lines (not shown in FIGS. 2A and 2B for the sake of clarity), the pumps 27, 28, 29, 37 (shown only schematically in FIGS. 2A and 2B), the valves 31, and the measuring cell 1. The fluidic region 45 can be closed on the front side by a housing door—which is, however, not shown in FIG. 2B—in order to allow a view of the schematically-shown interior of the housing 41 in the fluidic region 45.

The control system 39 is accommodated in the electronics region 43. In the present exemplary embodiment, the control system 39 is formed from several components arranged to be spatially separated from one another. These components include a first control unit 47 for the drives of the pumps 27, 28, 29, 37, a second control unit 48 for the measuring cell 1 and the optical sensor integrated into the measuring cell 1, a third control unit (not visible in FIGS. 2A and 2B) for controlling the valves 31 and optionally-provided further valves, and a higher-level data processing unit 49, e.g., a measuring transducer, a computer, or a memory-programmable logic controller. The first control unit 47 is connected via feedthroughs in the wall 42 to the pump drives for actuating the pumps. The second control unit 48 is also connected via feedthroughs in the wall 42 to the optical sensor belonging to the measuring cell 1.

The data processing unit 49 is connected to the other components of the control system 39 for communication, in order to effect, according to an operating program executed in the data processing unit 49, the operation of pumps, the optical sensor, and the valves in order to perform the analysis method described above. The data processing unit 49 is also connected to the optical sensor and/or to the second control unit 48 in order to detect measurement signals of the optical sensor. The data processing unit 49 also comprises the already-described evaluation program and is configured to execute the latter in order to determine measured values from measurement signals and output them via a display 50.

The walls 42 and 44 completely separate the fluidic region 45 from the electronics region 43 of the housing 41 in such a way that no liquid can enter the electronics region 43, even in the event of an unintended escape of liquid from the liquid lines, liquid containers, or the measuring cell. To this end, the walls 42 and 44 can seal the electronics region in a liquid-tight, or even splash-proof, manner. The risk of impairment of the electronics by unintentionally escaping liquid—particularly for the case where the sample feed line on the process side is under a high overpressure—is thus prevented.

The invention claimed is:

1. An analysis device for determining a measurand representing a silicate concentration in a sample liquid, the analysis device comprising:
    a housing divided into an electronics region and a fluidic region, wherein the electronics region is separated from the fluidic region by at least one wall;
    a measuring cell defining a vessel and disposed within the fluidic region;
    a sample feed line arranged within the fluidic region and opening into the vessel of the measuring cell, wherein the sample feed line is connected to an over-pressurized container containing the sample liquid, wherein the container is disposed outside the housing;
    at least one liquid container disposed within the fluidic region and containing a liquid;
    a liquid line arranged within the fluidic region, opening into the vessel of the measuring cell and connected to the at least one liquid container, wherein the liquid of the at least one liquid container is a reagent selected to react with the sample liquid to facilitate determining values of the measurand;
    a heater disposed within the fluidic region of the housing and arranged upstream of the measuring cell, wherein a portion of the sample feed line extends through the heater, and wherein the heater, the sample feed line and the liquid line are respectively configured such that the sample liquid in the sample feed line is heated by the heater while the liquid line bypasses the heater;
    at least one pump disposed within the fluidic region and configured to transport at least a portion of the liquid from the at least one liquid container into the vessel of the measuring cell;
    an optical sensor disposed within the fluidic region, the optical sensor including a radiation source and a radiation receiver, wherein the radiation source and the radiation receiver are arranged with respect to the measuring cell such that measuring radiation emitted by the radiation source passes through the vessel of the measuring cell and impinges on the radiation receiver;
    an electronic controller disposed within the electronics region and electrically connected to a drive of the at least one pump, to the radiation source and to the radiation receiver, the electronic controller configured to control the drive of the at least one pump for transporting liquid from the at least one liquid container into the measuring cell, to operate the radiation source for emitting measuring radiation, to detect electrical signals generated by the radiation receiver, and to determine the values of the measurand based upon the signals of the radiation receiver; and
    a flow meter arranged fluidically in the sample feed line and configured to detect a flow of the sample liquid through the sample feed line, wherein the flow meter is arranged upstream of the heater.

2. The analysis device of claim 1, wherein the at least one liquid container includes a plurality of liquid containers containing one liquid each, wherein all of the plurality of liquid containers are disposed within the fluidic region, and wherein the plurality of liquid containers are each connected to the measuring cell via a corresponding liquid line extending within the fluidic region.

3. The analysis device of claim 2, wherein the at least one pump includes a pump for each of the corresponding liquid lines connecting each of the plurality of liquid containers to the measuring cell such that each pump is connected to its corresponding liquid line and configured to transport liquid from the connected liquid container through the liquid line.

4. The analysis device of claim 3, wherein at least one of the plurality of liquid containers contains a standard solution containing silicate in a predetermined concentration, and wherein the pump connected to said liquid container via its corresponding liquid line is a peristaltic pump configured to transport standard solution to the measuring cell.

5. The analysis device of claim 2, wherein the liquid lines of the plurality of liquid containers are each configured to bypass the heater.

6. The analysis device of claim 1, further comprising a sample discharge line connected to the measuring cell and disposed within the fluidic region.

7. The analysis device of claim 6, wherein the measuring cell includes an overflow in fluid communication with the sample discharge line, the overflow establishing a maximum fill-level of the measuring cell such that, when the maximum fill-level in the measuring cell is reached, liquid passes from the vessel of the measuring cell via the overflow into the sample discharge line as to ensure that a predetermine amount of the sample liquid is present in the measuring cell.

8. The analysis device of claim 1, wherein the sample feed line includes a valve configured to selectively open or block the sample feed line to the flow of the sample liquid.

9. The analysis device of claim 1, further comprising a pressure reducer arranged fluidically between the sample feed line and the container containing the sample liquid.

10. The analysis device of claim 9, wherein the electronic controller is configured to control the pressure reducer based on a measurement signal from the flow meter.

11. The analysis device of claim 1, wherein the heater is a heat exchanger or resistance heater.

* * * * *